United States Patent
Heckel et al.

(10) Patent No.: US 11,179,371 B2
(45) Date of Patent: Nov. 23, 2021

(54) TRIAZOLE BENZAMIDE DERIVATIVES AS GPR142 AGONISTS

(71) Applicant: Boehringer Ingelheim International GmbH, Ingelheim am Rhein (DE)

(72) Inventors: Armin Heckel, Biberach an der Riss (DE); Robert Augustin, Biberach an der Riss (DE); Sebastian Bandholtz, Schemmerhofen (DE); Sara Frattini, Castelleone (IT); Bernd Wellenzohn, Friedrichshafen (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 17/251,576

(22) PCT Filed: Jun. 28, 2019

(86) PCT No.: PCT/EP2019/067344
§ 371 (c)(1),
(2) Date: Dec. 11, 2020

(87) PCT Pub. No.: WO2020/007729
PCT Pub. Date: Jan. 9, 2020

(65) Prior Publication Data
US 2021/0267947 A1 Sep. 2, 2021

(30) Foreign Application Priority Data
Jul. 4, 2018 (EP) .................................... 18181580

(51) Int. Cl.
A61K 31/4192 (2006.01)
C07D 403/04 (2006.01)

(52) U.S. Cl.
CPC ........ *A61K 31/4192* (2013.01); *C07D 403/04* (2013.01)

(58) Field of Classification Search
CPC ......................... C07D 403/04; A61K 31/4192
See application file for complete search history.

(56) References Cited

U.S. PATENT DOCUMENTS 8,889,665 B2 * 11/2014 Sapountzis .......... C07D 417/14
514/210.2

FOREIGN PATENT DOCUMENTS

| WO | 2018014800 | 1/2018 |
| WO | 2020007729 | 1/2020 |

OTHER PUBLICATIONS

International Search Report for PCT/EP2019/067344 dated Sep. 26, 2019.
Song, Triazolysalicylamides as potent Aurora kinase inhibitors, Bioorganic Chem and Medicincal Chem, vol. 22, 2014.
Alejandro, Natural History of cell adaptation and failure in type 2 diabetes, Moleucular aspectsof medicine, vol. 42, 2014.
Shimoda, The human glucagon like peptide-1 analogue, Diabetologica, 2011.
Gowda, Treatment with CNX-67, a novel GPR40 agonist, delays onset and progression of diabetes and improves beta cell preservation, BMC pharma and toxicology, 2013.
Moffett, Positive effects of GLP-1 receptor activation, Diabetes/Metabolism Research and Reviews, vol. 31, 2018.
Lin, GPR142 prompts glucagpn-like peptide-1 release from islets to improve B cell function, Molecular Melatvolism, vol. 11, 2018.
Lin, GPR142 controls tryptophan induced insulin and incretin hormone secretion to improve glucose metabolism, PLOS one, 2016.
Yu, Aminopyrazole-phenylanine based GPR142 agosnists, Medicinal Chem letters, vol. 4, 2013.
Guo, Discovery and Optimization of a novel Triamazole Series of GPR142 Agosnists, Medicinal Chem Letters, vol. 7, 2016.
Demaeyer, Plasma Tryptophan and five other amino acids in depressed and normal subjects, Arch gen. Psychiatry, Vo. 38, 1981.
Toda, Potent and Orally Bioavailable GPR 142 agonists as Novel Insulin Secretagogues, Medicinal Chem letters, vol. 4, 2013.
Kaushik, Insights into Unbound-Bound states of GPR142 receptor, Biomolecular Structure and Dynamics, 2017.
Murakoshi, Discovery and pharmacological effects of a novel GPR142 antagonist, J. of receptors and signal transduction, 2016.
Kaushik, Boolean network model for GPR142 against type 2 diabetes and relative dynaic change ratio analysis, 2015.
Du, Phenalynine derviatives as GPR142 agonists for the treatment of type 2 diabetes, Bioorganic and medicinal chem letters, 2012.
Wang, GPR142 agonists stimulate glucose dependent insulin secretion , PLOS one, 2016.

(Continued)

*Primary Examiner* — Kamal A Saeed
(74) *Attorney, Agent, or Firm* — David L. Kershner

(57) ABSTRACT

The present invention relates to compounds of general formula I,

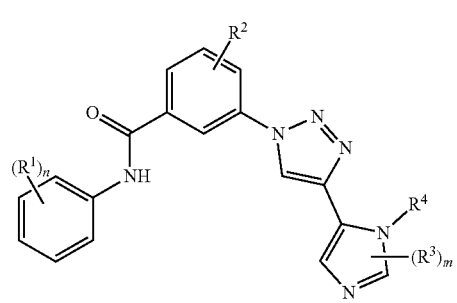

wherein the groups $R^1$, $R^2$, $R^3$, $R^4$, n and m are as defined herein, which have valuable pharmacological properties, in particular bind to the GPR142 receptor and modulate its activity. The compounds are suitable for treatment and prevention of diseases which can be influenced by this receptor, such as type 2 diabetes.

14 Claims, No Drawings

(56) References Cited

OTHER PUBLICATIONS

Wilson, Discovery and delvelopment of bez,o-{1,2,4}-triazolo-{1.4}-oxazepine GPR142 agonists, Bioorganic and Medicinal Chem letters, 2016.
Written OPinion for PCT/EP2019/067344 dated Oct. 9, 2019.
Lizarzaburu, Discovery and optiomization of a novel series of GPR142 agonists for the tretment of type 2 diabetes, Bioorganic and Medicinal Chem letters, 2012.

* cited by examiner

TRIAZOLE BENZAMIDE DERIVATIVES AS GPR142 AGONISTS

FIELD OF THE INVENTION

This invention relates to novel triazole benzamide derivatives, and pharmaceutically acceptable salts thereof, that are GPR142 agonists. In addition, the invention relates to processes for their preparation, to pharmaceutical compositions and combinations comprising said compounds and to their use in methods for the treatment of diseases which can be influenced by the activation of GPR142. Particularly, the pharmaceutical compositions of the invention are suitable for the treatment of type 2 diabetes.

BACKGROUND OF THE INVENTION

Type 2 diabetes is understood to evolve under circumstances of environmental risk factors and genetic predisposition from a combination of peripheral insulin resistance and pancreatic β-cell dysfunction. The disease represents a vicious cycle of increasing demands for insulin to be secreted in order to overcome insulin resistance driving a progressive decline of β-cell function and mass, ultimately leading to β-cell failure and insulin deficiency (Mol Aspects Med. (2014), 42, 19-41). The decline of β-cell function in type 2 diabetes is associated with a reduction in β-cell mass potentially caused by enhanced β-cell apoptosis and loss of β-cell proliferation.

Therapeutic principles for the treatment of type 2 diabetes include targeting GPCR signaling in pancreatic β-cells. GLP-1 analogues and GPR40 are examples for agonists of their respective G-protein coupled receptors, the GLP-1R and FFAR1, respectively. Those agents achieve glycemic control in humans and showed improved β-cell mass and function in animal models for type 2 diabetes (Diabetologia, (2011), 54(5), 1098-110, BMC Pharmacol Toxicol. (2013), 14, 28, Metab Res Rev, (2015), 31(3), 248-255).

GPR142 is a tryptophan-activated Gq-coupled receptor (Molecular Metabolism (2018), 11, 205-11), which is specifically expressed in pancreatic islets. Both natural (PLoS One, (2016) 11(6), e0157298) and synthetic (ACS Med Chem Lett, (2013) 4(9), 829-834, ACS Med Chem Lett. (2016), 7(12), 1107-11) ligands for this receptor enhance glucose-dependent insulin secretion and improve in vivo glucose homeostasis in animals. Therefore, small-molecule GPR142 agonists are potential agents suitable for the treatment of type 2 diabetes (Arch Gen Psychiatry, (2012) 38(6), 642-646, ACS Med Chem Lett, (2013) 4(8), 790-794, ACS Med Chem Lett, (2013) 4(9), 829-834, Syst Synth Biol, (2015) 9(1-2), 45-54, ACS Med Chem Lett, (2016) 7(12), 1107-1111, J Recept Signal Transduct Res, (2017) 37(3), 290-296, J Biomol Struct Dyn, (2018) 36(7), 1788-1805, Molecular Metabolism (2018), 11, 205-211). In addition to their insulinotropic action, defined as an increase of insulin-secretion in a glucose-dependent manner, synthetic GPR142 agonists induce proliferative and anti-apoptotic responses in β-cells from mouse and human dispersed pancreatic islets (Molecular Metabolism (2018), 11, 205-11). These observations suggest that synthetic GPR142 agonists are potentially useful for treating type 2 diabetes by improving glucose-dependent insulin secretion. In addition, GPR142 agonists might preserve pancreatic β-cell function in type 2 diabetic patients, making those agents in particular useful to prevent and treat the progression of the disease and its associated co-morbidities.

Low molecular weight GPR142 agonists are known in the art, for example, the compounds disclosed in WO 2008/045484; WO 2010/093849; WO 2015/120768; Bioorg Med Chem Lett, (2012) 22(19), 6218-6223; Bioorg Med Chem Lett, (2012) 22(18), 5942-5947; ACS Med Chem Lett, (2012) 4(8), 790-794; ACS Med Chem Lett, (2013) 4(9), 829-834; ACS Med Chem Lett, (2016), 7(12), 1107-1111; PLoS One, (2016) 11(6), e0157298; PLoS One, (2016), 11(4), e0154452; Bioorg Med Chem Lett, (2016) 26(12), 2947-2951; J Recept Signal Transduct Res, (2017), 37(3), 290-296 and Molecular Metabolism (2018), 11, 205-11.

The object of the present invention is to provide new compounds, hereinafter described as compounds of formula I, in particular new triazole benzamide derivatives, which are active with regard to GPR142, notably are agonists of GPR142.

A further object of the present invention is to provide new compounds, in particular new triazole benzamide derivatives, which have an activating effect on GPR142 in vitro and/or in vivo and possess suitable pharmacological and pharmacokinetic properties to use them as medicaments.

A further object of the present invention is to provide effective GPR142 agonists, in particular for the treatment of metabolic disorders, for example type 2 diabetes and type 2 diabetes-related diseases and conditions including diabetic ketoacidosis, hyperglycemia, diabetic neuropathy, diabetic retinopathy and related conditions such as obesity, the metabolic syndrome and polycystic ovary syndrome.

A further object of the present invention is to provide methods for treating a disease or condition mediated by the activation or GPR142 in a patient.

A further object of the present invention is to provide a pharmaceutical composition comprising at least one compound according to the invention.

A further object of the present invention is to provide a combination of at least one compound according to the invention with one or more additional therapeutic agents.

Further objects of the present invention become apparent to the one skilled in the art by the description hereinbefore and in the following and by the examples.

The triazole benzamide derivatives of the present invention may provide several advantages over those already known, such as enhanced potency, high metabolic and/or chemical stability, high selectivity and tolerability, enhanced solubility, and the possibility to form stable salts.

SUMMARY OF THE INVENTION

In a first aspect, the invention relates to a compound of formula

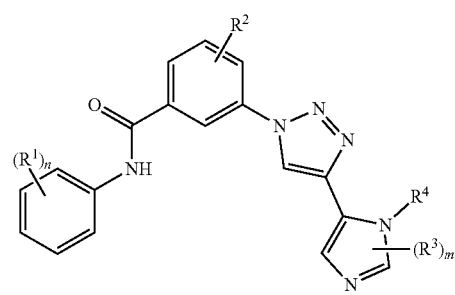

wherein $R^1$ is selected from the group $R^1$-G1 consisting of F, Cl, Br, I, CN, $NO_2$, $C_{1-3}$-alkyl, —O—($C_{1-4}$-alkyl), —COOH, —C(=O)—O—($C_{1-4}$-alkyl), —$NH_2$, —NH($C_{1-3}$-alkyl) and —N($C_{1-3}$-alkyl)$_2$, wherein each alkyl group or sub-group is optionally substituted with 1 or more F atoms; and wherein multiple $R^1$ may be identical or different if n is 2;

$R^2$ is selected from the group $R^2$-G1 consisting of H and $C_{1-3}$-alkyl;

$R^3$ is selected from the group $R^3$-G1 consisting of $C_{1-3}$-alkyl;

$R^4$ is selected from the group $R^4$-G1 consisting of $C_{1-3}$-alkyl;

n is an integer selected from 1 and 2; and m is an integer selected from 0 and 1;

wherein in any definition mentioned hereinbefore, if not specified otherwise, any alkyl group or sub-group may be straight-chained or branched and is optionally substituted with 1 or more F atoms, the isoforms, tautomers, stereoisomers, solvates, hydrates, and the salts thereof, particularly the pharmaceutically acceptable salts thereof with inorganic or organic acids or bases, or the combinations thereof.

The extension -Gn used within the definitions is meant to identify genus n of the respective substituent. For example, R-G1 defines genus 1 of the substituent R.

The expression "optionally substituted with 1 or more F atoms" means that none or one up to successively all H atoms bound to carbon atoms of the respective group or submoiety may be replaced by F atoms, preferably 1 to 5 H atoms or, more preferred, 1 to 3 H atoms may be replaced by F atoms.

In a further aspect this invention relates to a pharmaceutical composition, comprising one or more compounds of general formula I or one or more pharmaceutically acceptable salts thereof according to the invention, optionally together with one or more inert carriers and/or diluents.

In a further aspect this invention relates to a method for treating diseases or conditions which are mediated by activating GPR142 in a patient in need thereof characterized in that a compound of general formula I or a pharmaceutically acceptable salt thereof is administered to the patient.

According to another aspect of the invention, there is provided a method for treating type 2 diabetes and type 2 diabetes-related diseases and conditions including diabetic ketoacidosis, hyperglycemia, diabetic neuropathy, diabetic retinopathy and related conditions such as obesity, the metabolic syndrome and polycystic ovary syndrome in a patient in need thereof characterized in that a therapeutically effective amount of a compound of general formula I or a pharmaceutically acceptable salt thereof is administered to the patient.

According to another aspect of the invention, there is provided the use of a compound of the general formula I or a pharmaceutically acceptable salt thereof for the manufacture of a medicament for a therapeutic method as described hereinbefore and hereinafter.

According to another aspect of the invention, there is provided a compound of the general formula I or a pharmaceutically acceptable salt thereof for use in a therapeutic method as described hereinbefore and hereinafter.

In a further aspect this invention relates to a method for treating a disease or condition mediated by the activation of GPR142 in a patient that includes the step of administering to the patient in need of such treatment a therapeutically effective amount of a compound of the general formula I or a pharmaceutically acceptable salt thereof in combination with a therapeutically effective amount of one or more additional therapeutic agents.

In a further aspect this invention relates to the use of a compound of the general formula I or a pharmaceutically acceptable salt thereof in combination with one or more additional therapeutic agents for the treatment of diseases or conditions which are mediated by the activation of GPR142.

In a further aspect this invention relates to a pharmaceutical composition which comprises a compound according to general formula I or a pharmaceutically acceptable salt thereof and one or more additional therapeutic agents, optionally together with one or more inert carriers and/or diluents.

Other aspects of the invention become apparent to the one skilled in the art from the specification and the experimental part as described hereinbefore and hereinafter.

DETAILED DESCRIPTION OF THE INVENTION

Unless otherwise stated, the groups, residues, and substituents, particularly $R^1$, $R^2$, $R^3$, $R^4$, n and m are defined as above and hereinafter. If residues, substituents, or groups occur several times in a compound, such as $R^1$, they may have the same or different meanings. Some preferred meanings of individual groups and substituents of the compounds according to the invention will be given hereinafter. Any and each of these definitions may be combined with each other.

$R^1$:

$R^1$-G1:

The group $R^1$ is preferably selected from the group $R^1$-G1 as defined hereinbefore.

$R^1$-G2:

In another embodiment, the group $R^1$ is independently of each other selected from the group $R^1$-G2 consisting of F, Cl, Br, CN, $NO_2$, $C_{1-2}$-alkyl, —O—($C_{1-3}$-alkyl), —C(=O)—O—($C_{1-2}$-alkyl) and —N($C_{1-2}$-alkyl)$_2$, wherein each alkyl group or sub-group is optionally substituted with one or more F atoms.

$R^1$-G3:

In another embodiment, the group $R^1$ is independently of each other selected from the group $R^1$-G3 consisting of F, Cl, Br, CN, $NO_2$, $CH_3$, —O—($C_{1-2}$-alkyl), —C(=O)—O—$CH_3$ and —N($CH_3$)$_2$, wherein each alkyl group or sub-group is optionally substituted with one to three F atoms.

$R^1$-G4:

In another embodiment, the group $R^1$ is independently of each other selected from the group $R^1$-G4 consisting of F, Cl, Br, CN, $NO_2$, $CH_3$, $CF_3$, —O—$CH_3$, —O—$CF_3$, —O—$CHF_2$, —O—$CF_2$—$CHF_2$, —C(=O)—O—$CH_3$ and —N($CH_3$)$_2$.

$R^1$-G5:

In another embodiment, the group $R^1$ is independently of each other selected from the group $R^1$-G5 consisting of F, Cl, Br, $NO_2$, $CH_3$, $CF_3$, —O—$CF_3$ and —O—$CHF_2$.

$R^2$:

$R^2$-G1:

The group $R^2$ is preferably selected from the group $R^2$-G1 as defined hereinbefore.

$R^2$-G2:

In another embodiment, the group $R^2$ is selected from the group $R^2$-G2 consisting of H and $CH_3$.

$R^2$-G3:

In another embodiment, the group $R^2$ is selected from the group $R^2$-G3 consisting of $CH_3$.

R²-G4:

In another embodiment, the group R² is selected from the group R²-G4 consisting of H.

R³:

R³-G1:

The group R³ is preferably selected from the group R³-G1 as defined hereinbefore.

R³-G2:

In another embodiment, the group R³ is selected from the group R³-G2 consisting of $CH_3$.

R⁴:

R⁴-G1:

The group R⁴ is preferably selected from the group R⁴-G1 as defined hereinbefore.

R⁴-G2:

In another embodiment, the group R⁴ is selected from the group R⁴-G2 consisting of $CH_3$.

n:

n is an integer selected from 1 and 2.

Preferably, n is 2.

More preferably, n is 1.

m:

n is an integer selected from 0 and 1.

Preferably, m is 1.

More preferably, m is 0.

The following preferred embodiments of compounds of the formula I are described using generic formulae I.1, I.2, I.3 and I.4, wherein any tautomers, solvates, hydrates and salts thereof, in particular the pharmaceutically acceptable salts thereof, are encompassed.

Examples of preferred subgeneric embodiments (E) according to the present invention are set forth in the following Table 1, wherein each substituent group of each embodiment is defined according to the definitions set forth hereinbefore. For example, the entry -G1 in the column under R¹— and in the line of E1 means that in embodiment E1 substituent R¹ is selected from the definition designated R¹-G1. The same applies analogously to the other variables incorporated in the general formulae.

TABLE 1

| E | Formula | R¹— | R²— | R³— | R⁴— | n | m |
|---|---|---|---|---|---|---|---|
| E1 | I | -G1 | -G1 | -G1 | -G1 | 1 or 2 | 0 or 1 |
| E2 | I | -G1 | -G1 | -G2 | -G2 | 1 | 0 |
| E3 | I | -G1 | -G2 | -G2 | -G2 | 1 or 2 | 0 or 1 |
| E4 | I | -G1 | -G2 | -G2 | -G2 | 1 | 0 |
| E5 | I | -G1 | -G3 | -G2 | -G2 | 1 or 2 | 0 or 1 |
| E6 | I | -G1 | -G3 | -G2 | -G2 | 1 | 0 |
| E7 | I | -G1 | -G4 | -G2 | G2 | 1 or 2 | 0 or 1 |
| E8 | I | -G1 | -G4 | -G2 | -G2 | 1 | 0 |
| E9 | I | -G2 | -G2 | -G2 | -G2 | 1 or 2 | 0 or 1 |
| E10 | I | -G2 | -G2 | -G2 | -G2 | 1 | 0 |
| E11 | I | -G2 | -G3 | -G2 | -G2 | 1 or 2 | 0 or 1 |
| E12 | I | -G2 | -G3 | -G2 | -G2 | 1 | 0 |
| E13 | I | -G2 | -G4 | -G2 | -G2 | 1 or 2 | 0 or 1 |
| E14 | I | -G2 | -G4 | -G2 | -G2 | 1 | 0 |
| E15 | I | -G3 | -G2 | -G2 | -G2 | 1 or 2 | 0 or 1 |
| E16 | I | -G3 | -G2 | -G2 | -G2 | 1 | 0 |
| E17 | I | -G3 | -G3 | -G2 | -G2 | 1 or 2 | 0 or 1 |
| E18 | I | -G3 | -G3 | -G2 | -G2 | 1 | 0 |
| E19 | I | -G3 | -G3 | -G2 | -G2 | 1 or 2 | 0 or 1 |
| E20 | I | -G3 | -G4 | -G2 | -G2 | 1 | 0 |
| E21 | I | -G4 | -G2 | -G2 | -G2 | 1 or 2 | 0 or 1 |
| E22 | I | -G4 | -G2 | -G2 | -G2 | 1 | 0 |
| E23 | I | -G4 | -G3 | -G2 | -G2 | 1 or 2 | 0 or 1 |
| E24 | I | -G4 | -G3 | -G2 | -G2 | 1 | 0 |
| E25 | I | -G4 | -G4 | -G2 | -G2 | 1 or 2 | 0 or 1 |
| E26 | I | -G4 | -G4 | -G2 | -G2 | 1 | 0 |
| E27 | I | -G5 | -G2 | -G2 | -G2 | 1 or 2 | 0 or 1 |
| E28 | I | -G5 | -G2 | -G2 | -G2 | 1 | 0 |
| E29 | I | -G5 | -G3 | -G2 | -G2 | 1 or 2 | 0 or 1 |
| E30 | I | -G5 | -G3 | -G2 | -G2 | 1 | 0 |
| E31 | I | -G5 | -G4 | -G2 | -G2 | 1 or 2 | 0 or 1 |
| E32 | I | -G5 | -G4 | -G2 | -G2 | 1 | 0 |
| E33 | I.1 | -G1 | -G1 | -G1 | -G1 | 1 or 2 | 0 or 1 |
| E34 | I.1 | -G2 | -G2 | -G2 | -G2 | 1 or 2 | 0 or 1 |
| E35 | I.1 | -G3 | -G3 | -G2 | -G2 | 1 or 2 | 0 or 1 |
| E36 | I.1 | -G4 | -G4 | -G2 | -G2 | 1 or 2 | 0 |
| E37 | I.1 | -G5 | -G4 | -G2 | -G2 | 1 or 2 | 0 |
| E38 | I.4 | -G3 | — | -G2 | -G2 | — | 0 or 1 |
| E39 | I.4 | -G5 | — | -G2 | -G2 | — | 0 or 1 |

Particularly preferred compounds, including their tautomers and stereoisomers, the salts thereof, or any solvates or hydrates thereof, are described in the experimental section hereinafter.

Terms and Definitions

Terms not specifically defined herein should be given the meanings that would be given to them by one of skill in the art in light of the disclosure and the context. As used in the specification, however, unless specified to the contrary, the following terms have the meaning indicated and the following conventions are adhered to.

The terms "compound(s) according to this invention", "compound(s) of formula (I)", "compound(s) of the invention" and the like denote the compounds of the formula (I) according to the present invention including their tautomers, stereoisomers and mixtures thereof and the salts thereof, in particular the pharmaceutically acceptable salts thereof, and the solvates and hydrates of such compounds, including the solvates and hydrates of such tautomers, stereoisomers and salts thereof.

The terms "treatment" and "treating" embrace both preventative, i.e. prophylactic, or therapeutic, i.e. curative and/or palliative, treatment. Thus the terms "treatment" and "treating" comprise therapeutic treatment of patients having already developed said condition, in particular in manifest form. Therapeutic treatment may be symptomatic treatment in order to relieve the symptoms of the specific indication or causal treatment in order to reverse or partially reverse the conditions of the indication or to stop or slow down progression of the disease. Thus the compositions and methods of the present invention may be used for instance as therapeutic treatment over a period of time as well as for chronic therapy. In addition the terms "treatment" and "treating" comprise prophylactic treatment, i.e. a treatment of patients at risk to develop a condition mentioned hereinbefore, thus reducing said risk.

When this invention refers to patients requiring treatment, it relates primarily to treatment in mammals, in particular humans.

The term "therapeutically effective amount" means an amount of a compound of the present invention that (i) treats or prevents the particular disease or condition, (ii) attenuates, ameliorates, or eliminates one or more symptoms of the particular disease or condition, or (iii) prevents or delays the onset of one or more symptoms of the particular disease or condition described herein.

The terms "modulated" or "modulating", or "modulate(s)", as used herein, unless otherwise indicated, refer to the activation of the G-protein-coupled receptor GPR40 with one or more compounds of the present invention.

The terms "mediated" or "mediating" or "mediate", as used herein, unless otherwise indicated, refer to the (i) treatment, including prevention of the particular disease or condition, (ii) attenuation, amelioration, or elimination of one or more symptoms of the particular disease or condition, or (iii) prevention or delay of the onset of one or more symptoms of the particular disease or condition described herein.

The term "substituted" as used herein, means that any one or more hydrogens on the designated atom, radical or moiety is replaced with a selection from the indicated group, provided that the atom's normal valence is not exceeded, and that the substitution results in an acceptably stable compound.

In the groups, radicals, or moieties defined below, the number of carbon atoms is often specified preceding the group, for example, $C_{1-6}$-alkyl means an alkyl group or radical having 1 to 6 carbon atoms. In general, for groups comprising two or more subgroups, the last named subgroup is the radical attachment point, for example, the substituent "aryl-$C_{1-3}$-alkyl-" means an aryl group which is bound to a $C_{1-3}$-alkyl-group, the latter of which is bound to the core or to the group to which the substituent is attached.

In case a compound of the present invention is depicted in form of a chemical name and as a formula in case of any discrepancy the formula shall prevail.

An asterisk may be used in sub-formulas to indicate the bond which is connected to the core molecule as defined.

The numeration of the atoms of a substituent starts with the atom which is closest to the core or to the group to which the substituent is attached.

For example, the term "3-carboxypropyl-group" represents the following substituent:

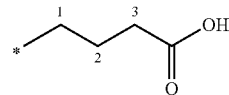

wherein the carboxy group is attached to the third carbon atom of the propyl group. The terms "1-methylpropyl-", "2,2-dimethylpropyl-" or "cyclopropylmethyl-" group represent the following groups:

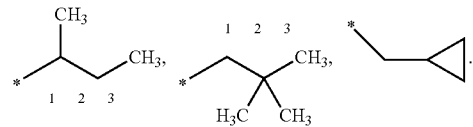

The asterisk may be used in sub-formulas to indicate the bond which is connected to the core molecule as defined.

In a definition of a group the term "wherein each X, Y and Z group is optionally substituted with" and the like denotes that each group X, each group Y and each group Z either each as a separate group or each as part of a composed group may be substituted as defined. For example a definition "$R^{ex}$ denotes H, $C_{1-3}$-alkyl, $C_{3-6}$-cycloalkyl, $C_{3-6}$-cycloalkyl-$C_{1-3}$-alkyl or $C_{1-3}$-alkyl-O—, wherein each alkyl group is optionally substituted with one or more $L^{ex}$." or the like means that in each of the beforementioned groups which comprise the term alkyl, i.e. in each of the groups $C_{1-3}$-alkyl, $C_{3-6}$-cycloalkyl-$C_{1-3}$-alkyl and $C_{1-3}$-alkyl-O—, the alkyl moiety may be substituted with $L^{ex}$ as defined.

Unless specifically indicated, throughout the specification and the appended claims, a given chemical formula or name shall encompass tautomers and all stereo, optical and geometrical isomers (e.g. enantiomers, diastereomers, E/Z isomers etc . . . ) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, and commensurate with a reasonable benefit/risk ratio.

As used herein, "pharmaceutically acceptable salts" refer to derivatives of the disclosed compounds wherein the parent compound is modified by making acid or base salts thereof.

Salts of other acids than those mentioned above which for example are useful for purifying or isolating the compounds of the present invention (e.g. trifluoro acetate salts) also comprise a part of the invention.

The term halogen generally denotes fluorine, chlorine, bromine and iodine.

The term "$C_{1-n}$-alkyl", wherein n is an integer from 1 to n, either alone or in combination with another radical denotes an acyclic, saturated, branched or linear hydrocarbon radical with 1 to n C atoms. For example the term $C_{1-5}$-alkyl embraces the radicals H₃C—, H₃C—CH₂—, H₃C—CH₂—CH₂—, H₃C—CH(CH₃)—, H₃C—CH₂—CH₂—CH₂—, H₃C—CH₂—CH(CH₃)—, H₃C—CH(CH₃)—CH₂—, H₃C—C(CH₃)₂—, H₃C—CH₂—CH₂—CH₂—CH₂—, H₃C—CH₂—CH₂—CH(CH₃)—, H₃C—CH₂—CH(CH₃)—CH₂—, H₃C—CH(CH₃)—CH₂—CH₂—, H₃C—CH₂—C(CH₃)₂—, H₃C—C(CH₃)₂—CH₂—, H₃C—CH(CH₃)—CH(CH₃)— and H₃C—CH₂—CH(CH₂CH₃)—.

The term "$C_{2-n}$-alkynyl", is used for a group as defined in the definition for "$C_{1-n}$-alkyl" with at least two carbon atoms, if at least two of those carbon atoms of said group are bonded to each other by a triple bond. For example the term $C_{2-3}$-alkynyl includes —C≡CH, —C≡C—CH₃, —CH₂—C≡CH.

Many of the terms given above may be used repeatedly in the definition of a formula or group and in each case have one of the meanings given above, independently of one another.

Biological Methods
Pharmacological Activity

The activity of the compounds of the invention may be demonstrated using the following assay which determines the generation of inositol monophosphate, which is a stable metabolite of IP3 induced by activation of a phospholipase C (PLC). This assay allows monitoring activity of compounds acting on Gq-coupled receptors. The principle of the assay is based on the competition between IP1 generated in the cells with d2-labeled IP1 for binding to a monoclonal anti-IP1 Tb2+ cryptate that allows for measuring quantitative changes using the Homogeneous Time Resolved Fluorescence. LiCl is added to the cell stimulation buffer, causing IP1 to accumulate upon receptor activation.

The open reading frame encoding the human GPR142 receptor (primary accession number: NM_181790; Gene ID: 350383) was cloned into the pcDNA5/FRT/TO vector for stable, and inducible expression using the Flp-In™ T-REx™ technology in HEK293 FLPinTREX cells. For stable expression, HEK293 FLPinTREX cells were co-transfected with the vector encoding human GPR142 and the pOG44 plasmid that constitutively expresses the Flp recombinase for stable integration of the human GPR142 into the genome of the Flp-In™ T-REx™ host cell line. Stably expressing clones were obtained by hygromycin (100 µg/ml) selection. To test for GPR142 agonist activity the human GPR142 receptor cell clone was thawed at 37° C. and immediately diluted with cell culture medium (Hams F12 medium; 10% FBS, 15 µg/ml Blasticidin, 100 µg/ml Hygromycin B). After centrifugation, the cell pellet was resuspended in medium, and distributed into the assay well plates (10000 cells/well; 20 µl/well). Receptor expression was induced by adding 0.1 µg/ml Doxycyclin to the culture medium. The plates were incubated for one hour at room temperature, followed by a 24 hours incubation at 37° C./5% CO₂. After washing the cells in the plate twice with 60 µl assay buffer (10 mM HEPES, 1 mM CaCl₂, 0.5 mM MgCl₂, 4.2 mM KCl, 146 mM NaCl, 5.5 mM Glucose, 50 mM LiCl and 0.1% BSA, pH 7.4; 20 µl buffer remained in the wells after washing), 10 µl per well of test compound diluted in assay buffer was added to the wells. The assay plate was incubated for 60 minutes at 37° C. Then 5 µl per well of Anti-IP1-Cryptate Tb solution (prepared by 1:33 dilution of stock with Lysis buffer from IP-One Kit) and 5 µl per well of IP1-d2 (Prepared by 1:33 dilution of stock with Lysis buffer from IP-One Kit) dilution were added, followed by another 60 minutes incubation (light protected, room temperature). The emissions at 615 nm and 665 nm (excitation wavelength: 320 nm) were measured on the EnVision™ reader (PerkinElmer). The ratio between the emission at 665 nm and 615 was calculated by the reader.

Each assay microtiter plate contained 8 wells in with vehicle controls instead of compound (100% CTL; low values, negative control) and 8 wells with a reference GPR142 agonist (200% CTL; high values; positive control). An IP1 standard curve was prepared according to the manufacturer.

The ratio between the emission at 665 nm and the emission at 615 nm (Em665/Em615 ratio) was calculated and the signals for the test items were normalized using the positive and negative controls by the following formula: 100−(100×[(ratio(sample)−ratio(low))/(ratio(high)−ratio(low))].

$EC_{50}$ values for compounds according to the invention are shown in the following table. The number of the compound corresponds to the number of the Example in the experimental section.

| Example | $EC_{50}$ (nM) | Example | $EC_{50}$ (nM) |
|---|---|---|---|
| 1 | 0.40 | 11 | 0.74 |
| 2 | 0.05 | 12 | 0.73 |
| 3 | 0.21 | 13 | 0.85 |
| 4 | 0.47 | 14 | 0.86 |
| 5 | 0.37 | 15 | <0.38 |
| 6 | 0.21 | 16 | <0.38 |
| 7 | 0.37 | 17 | 0.95 |
| 8 | 0.63 | 18 | 0.64 |
| 9 | 0.45 | 19 | <0.38 |
| 10 | <0.38 | 20 | 0.64 |

In view of their ability to modulate the activity of GPR142, in particular an agonistic activity, the compounds of general formula I according to the invention, including the corresponding salts thereof, are theoretically suitable for the treatment of all those diseases or conditions which may be affected or which are mediated by the activation of GPR142.

Accordingly, the present invention relates to a compound of general formula I as a medicament.

Furthermore, the present invention relates to the use of a compound of general formula I or a pharmaceutical composition according to this invention for the treatment and/or prevention of diseases or conditions which are mediated by the activation of GPR142 in a patient, preferably in a human.

In yet another aspect the present invention relates to a method for treating a disease or condition mediated by the activation of GPR142 in a mammal that includes the step of administering to a patient, preferably a human, in need of such treatment a therapeutically effective amount of a compound or a pharmaceutical composition of the present invention.

Diseases and conditions mediated by agonists of GPR142 embrace conditions of relative insulin deficiency such as type 2 diabetes and associated diseases such as type 2 diabetes and type 2 diabetes-related diseases and conditions including diabetic ketoacidosis, hyperglycemia, diabetic neuropathy, diabetic retinopathy and related conditions such as obesity, the metabolic syndrome and polycystic ovary syndrome.

In particular, the compounds and pharmaceutical compositions according to the invention are suitable for the treatment of relative insulin deficiency in type 2 diabetic patients by increasing glucose stimulated insulin secretion from the pancreatic β-cell The compounds according to the invention are most particularly suitable for treating the progression of type 2 diabetes potentially by improving β-cell function inhibiting β-apoptosis and increasing β-cell proliferation.

The dose range of the compounds of general formula I applicable per day is usually from 0.001 to 10 mg per kg body weight, for example from 0.01 to 8 mg per kg body weight of the patient. Each dosage unit may conveniently contain from 0.1 to 1000 mg, for example 0.5 to 500 mg.

The actual therapeutically effective amount or therapeutic dosage will of course depend on factors known by those skilled in the art such as age and weight of the patient, route of administration and severity of disease. In any case the compound or composition will be administered at dosages and in a manner which allows a therapeutically effective amount to be delivered based upon patient's unique condition.

The compounds, compositions, including any combinations with one or more additional therapeutic agents, according to the invention may be administered by oral, transdermal, inhalative, parenteral or sublingual route. Of the possible methods of administration, oral or intravenous administration is preferred.

Pharmaceutical Compositions

Suitable preparations for administering the compounds of formula I, optionally in combination with one or more further therapeutic agents, will be apparent to those with ordinary skill in the art and include for example tablets, pills, capsules, suppositories, lozenges, troches, solutions, syrups, elixirs, sachets, injectables, inhalatives and powders etc. Oral formulations, particularly solid forms such as e.g. tablets or capsules are preferred. The content of the pharmaceutically active compound(s) is advantageously in the range from 0.1 to 90 wt.-%, for example from 1 to 70 wt.-% of the composition as a whole.

Suitable tablets may be obtained, for example, by mixing one or more compounds according to formula I with known excipients, for example inert diluents, carriers, disintegrants, adjuvants, surfactants, binders and/or lubricants. The tablets may also consist of several layers. The particular excipients, carriers and/or diluents that are suitable for the desired preparations will be familiar to the skilled man on the basis of his specialist knowledge. The preferred ones are those that are suitable for the particular formulation and method of administration that are desired. The preparations or formulations according to the invention may be prepared using methods known per se that are familiar to the skilled man, such as for example by mixing or combining at least one compound of formula I according to the invention, or a pharmaceutically acceptable salt of such a compound, and one or more excipients, carriers and/or diluents.

Combination Therapy

The compounds of the invention may further be combined with one or more, preferably one additional therapeutic agent. According to one embodiment the additional therapeutic agent is selected from the group of therapeutic agents useful in the treatment of diseases or conditions described hereinbefore, in particular associated with type 2 diabetes and its associated micro- and macrovascular complications such as diabetic retinopathy, diabetic neuropathy, diabetic kidney disease, and cardiovascular diseases, respectively. Additional therapeutic agents which are suitable for such combinations include in particular those which for example potentiate the therapeutic effect of one or more active substances with respect to one of the indications mentioned and/or which allow the dosage of one or more active substances to be reduced.

Therefore a compound of the invention may be combined with one or more additional therapeutic agents selected from the group consisting of Metformin, DPPIV inhibitors, SGLT-2 inhibitors, agonists for the GLP-1R, GIPR and GCGR and combinations thereof, GPR40 (FFAR1) agonists, and FGF-21 analogues.

Linagliptin (DPPIV), Empagliflozin (SGLT2i), GLP-1R agonist (Liraglutide, Dulaglutide) are specific agents representing examples are for their class of approved and marketed medications for the treatment of type 2 diabetes.

The dosage for the combination partners mentioned above is usually ⅕ of the lowest dose normally recommended up to 1/1 of the normally recommended dose.

Therefore, in another aspect, this invention relates to the use of a compound according to the invention in combination with one or more additional therapeutic agents described hereinbefore and hereinafter for the treatment of diseases or conditions which may be affected or which are mediated by the activation of GPR142, in particular diseases or conditions as described hereinbefore and hereinafter.

In yet another aspect the present invention relates a method for treating a disease or condition mediated by the activation of GPR142 in a patient that includes the step of administering to the patient, preferably a human, in need of such treatment a therapeutically effective amount of a compound of the present invention in combination with a therapeutically effective amount of one or more additional therapeutic agents described in hereinbefore and hereinafter, The use of the compound according to the invention in combination with the additional therapeutic agent may take place simultaneously or at staggered times.

The compound according to the invention and the one or more additional therapeutic agents may both be present together in one formulation, for example a tablet or capsule, or separately in two identical or different formulations, for example as a so-called kit-of-parts.

Consequently, in another aspect, this invention relates to a pharmaceutical composition which comprises a compound according to the invention and one or more additional therapeutic agents described hereinbefore and hereinafter, optionally together with one or more inert carriers and/or diluents.

Other features and advantages of the present invention will become apparent from the following more detailed Examples which illustrate, by way of example, the principles of the invention.

Synthesis

The compounds according to the invention and their intermediates may be obtained using methods of synthesis which are known to the one skilled in the art and described in the literature of organic synthesis for example using methods described in "Comprehensive Organic Transformations", $2^{nd}$ Edition, Richard C. Larock, John Wiley & Sons, 2010, and "March's Advanced Organic Chemistry", 7th Edition, Michael B. Smith, John Wiley & Sons, 2013. Preferably the compounds are obtained analogously to the methods of preparation explained more fully hereinafter, in particular as described in the experimental section. In some cases the sequence adopted in carrying out the reaction schemes may be varied. Variants of these reactions that are known to the skilled man but are not described in detail here may also be used. The general processes for preparing the compounds according to the invention will become apparent to the skilled man on studying the schemes that follow. Starting compounds are commercially available or may be prepared by methods that are described in the literature or herein, or may be prepared in an analogous or similar manner. Before the reaction is carried out, any corresponding functional groups in the starting compounds may be protected using conventional protecting groups. These protecting groups may be cleaved again at a suitable stage within the reaction sequence using methods familiar to the skilled man and described in the literature for example in "Protecting Groups", 3$^{rd}$ Edition, Philip J. Kocienski, Thieme, 2005, and "Protective Groups in Organic Synthesis", 4th Edition, Peter G. M. Wuts, Theodora W. Greene, John Wiley & Sons, 2006.

pyridine, 4-dimethylaminopyridine etc.) to form an amide bond; $R^1$, $R^2$, $R^3$, $R^4$, m and n in Scheme 1 have the meanings as defined hereinbefore. Alternatively, the carboxylic acid is transformed into a carboxylic chloride (using, e.g., oxalyl choride or thionyl chloride in dichloromethane) and coupled as such with amine (III) in the presence of a suitable base (e.g. triethylamine, N,N-diisopropylethylamine, pyridine etc.).

In case amine (III) is employed with a protected or masked amino group on the benzene ring, this group can be transformed afterwards into an $NH_2$ group by cleaving off the protective group applying standard procedures reported in the literature of organic chemistry. A tert-butyl ester is preferably cleaved under acidic conditions with, e.g. trifluoroacetic acid or hydrochloric acid, in a solvent such as dichloromethane, 1,4-dioxane, isopropanol, or ethyl acetate. A benzyl group can be removed by using hydrogen in the presence of a transition metal such as palladium on carbon. Benzyl groups bearing electron donating groups such as methoxy on the aromatic ring may also be removed under oxidative conditions (e.g. with ceric ammonium nitrate (CAN) or 2,3-dichloro-5,6-dicyanoquinone (DDQ)) or acidic conditions (e.g. with trifluoroacetic acid or hydrochloric acid).

In case amine (III) is employed with a carboxylic ester group on the benzene ring, this can be transformed afterwards into a COOH group by cleaving the ester group applying standard procedures reported in the literature of organic chemistry (see below).

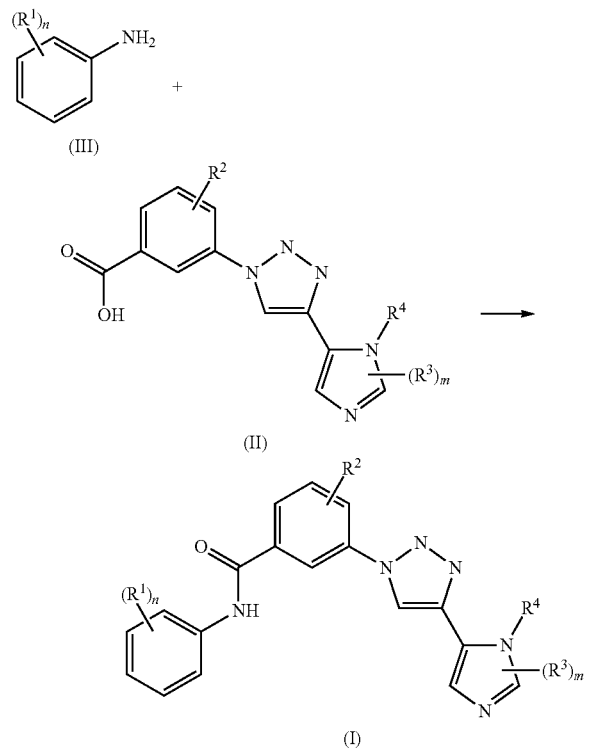

Scheme 1

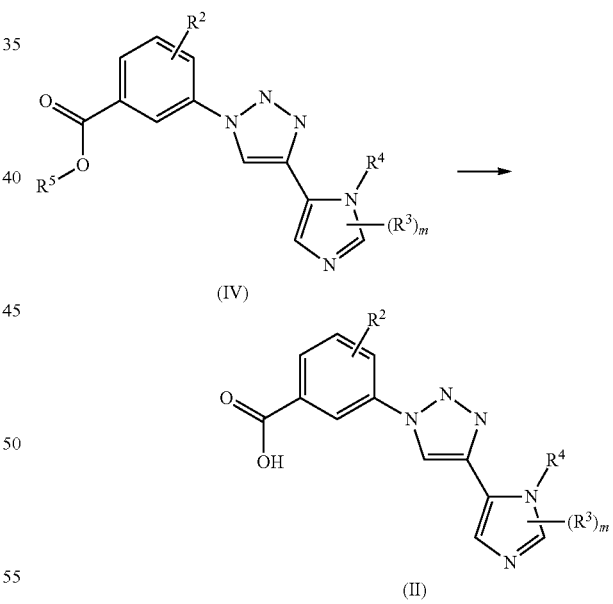

Scheme 2

Scheme 1: Compounds of formula (I) can be prepared by the reaction of a suitable acid of formula (II) (either as a free acid or as a salt with a suitable metal cation such as Li$^+$, Na$^+$, K$^+$ etc.) and a suitable amine of formula (III) (either as a free amine or as a salt such as a hydrochloride, hydrobromide etc.) in a suitable solvent (e.g. dichloromethane, tetrahydrofuran, 1,4-dioxane, N,N-dimethylformamide, N,N-dimethylacetamide, 1-methyl-2-pyrrolidinone etc.) in the presence of a suitable coupling agent (e.g. O-(7-azabenzotriazol-1-yl)-N,N,N',N'-tetramethyluronium-hexafluorophosphate (HATU), O-(benzotriazol-1-yl)-N,N,N',N'-tetramethyluronium tetrafluoroborate (TBTU), (benzotriazol-1-yloxy)tripyrrolidinophosphonium hexafluorophosphate (PyBOP), 3-dimethylamino-propyl)-ethyl-carbodiimide (EDC) etc.) and a base (e.g. triethylamine, N,N-diisopropylethylamine, Scheme 2: Acids of formula (II), wherein $R^2$, $R^3$, $R^4$ and m have the meanings as defined hereinbefore, are preferably prepared from the corresponding ester (IV) through hydrolysis or hydrogenolysis depending on the nature of $R^5$. Lower alkyl group esters such as ethyl or methyl esters are preferably cleaved by hydrolysis with a hydroxide base such as NaOH, LiOH or KOH in a mixture of water and a suitable miscible solvent (e.g., tetrahydrofuran, methanol, ethanol, 1,4-dioxane etc. or mixtures of these), with heating if necessary. The acid may be isolated either as a salt with the metal cation or as a free acid. tert-Butyl ester is preferably cleaved by treatment with an acid (e.g. hydrochloric acid or trifluoroacetic acid) in a suitable solvent (e.g., dichloromethane, 1,4-dioxane, methanol, ethanol, tetrahydrofuran, water or mixtures of these). A benzyl ester is preferably cleaved by hydrogenolysis with a suitable catalyst (e.g., palladium on carbon etc.) in a suitable solvent (e.g. ethanol, methanol, tetrahydrofuran, dichloromethane, ethyl acetate etc.) under an atmosphere of hydrogen (preferably 1 to 5 bar).

Scheme 3

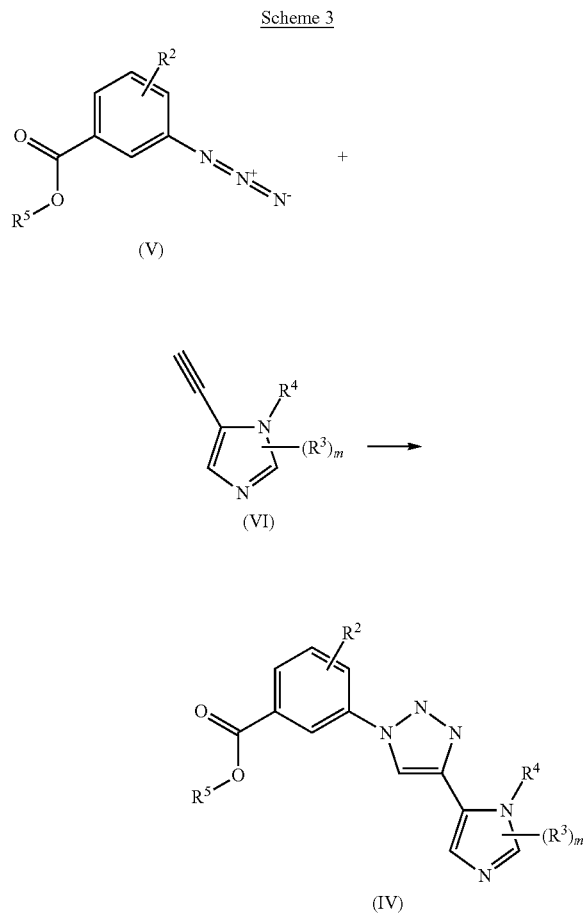

Scheme 3: Triazoles of formula (IV), wherein $R^2$, $R^3$, $R^4$, $R^5$ and m have the meanings defined hereinbefore, can be prepared from an azide (V) by reaction with a suitable alkyne derivative (VI) under copper mediated catalytic conditions (e.g. catalytic copper(II) sulfate and sodium ascorbate in a mixture of water and methanol or tert-butanol).

Scheme 4

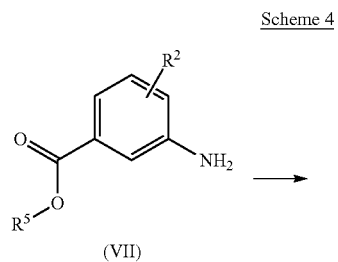

-continued

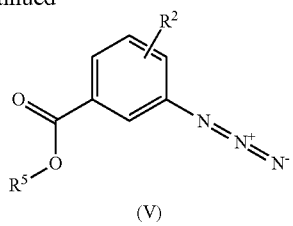

Scheme 4: Azides of formula (V), wherein $R^2$ and $R^5$ have the meanings defined hereinbefore, can be obtained from an aniline of formula (VII) by the reaction with sodium nitrite in water in the presence of a suitable acid such as hydrochloric acid and subsequent treatment with sodium azide.

Scheme 5

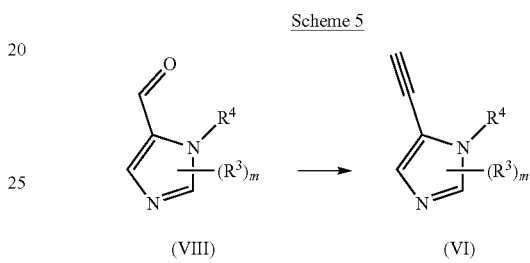

Scheme 5: Alkyne derivatives of formula (IV), wherein $R^3$, $R^4$ and m have the meanings defined hereinbefore, can be prepared from an aldehyde (VIII) by reaction with dimethyl (1-diazo-2-oxopropyl)phosphonate (Bestmann-Ohira reagent) in the presence of a base (e.g. $Cs_2CO_3$ or $K_2CO_3$) in methanol or a suitable solvent mixture such as methanol/tetrahydrofuran.

The compounds of formula (I) may be resolved into their enantiomers and/or diastereomers as mentioned below. Thus, for example, cis/trans mixtures may be resolved into their cis and trans isomers and racemic compounds may be separated into their enantiomers.

The cis/trans mixtures may be resolved, for example, by chromatography into the cis and trans isomers thereof. The compounds of formula (I) which occur as racemates may be separated by methods known per se into their optical antipodes and diastereomeric mixtures of compounds of general formula (I) may be resolved into their diastereomers by taking advantage of their different physicochemical properties using methods known per se, e.g. chromatography and/or fractional crystallization; if the compounds obtained thereafter are racemates, they may be resolved into the enantiomers as mentioned below.

The racemates are preferably resolved by column chromatography on chiral phases or by crystallization from an optically active solvent or by reacting with an optically active substance which forms salts or derivatives such as esters or amides with the racemic compound. Salts may be formed with enantiomerically pure acids for basic compounds and with enantiomerically pure bases for acidic compounds. Diastereomeric derivatives are formed with enantiomerically pure auxiliary compounds, e.g. acids, their activated derivatives, or alcohols. Separation of the diastereomeric mixture of salts or derivatives thus obtained may be achieved by taking advantage of their different physicochemical properties, e.g. differences in solubility; the free antipodes may be released from the pure diastereomeric salts or derivatives by the action of suitable agents. Optically active acids commonly used for such a purpose as well as optically active alcohols applicable as auxiliary residues are known to those skilled in the art.

As mentioned above, the compounds of formula (I) may be converted into salts, particularly for pharmaceutical use into the pharmaceutically acceptable salts. As used herein, "pharmaceutically acceptable salts" refer to derivatives of the disclosed compounds wherein the parent compound is modified by making acid or base salts thereof.

The compounds according to the invention are advantageously also obtainable using the methods described in the examples that follow, which may also be combined for this purpose with methods known to the skilled man from the literature.

EXAMPLES/PRELIMINARY REMARKS

The terms "ambient temperature" and "room temperature" are used interchangeably and designate a temperature of about 20° C., e.g. 15 to 25° C.

As a rule, $^1$H-NMR and/or mass spectra have been obtained for the compounds prepared.

Unless otherwise specified, compounds containing chiral centers have the stereochemistry depicted. The assignment of stereochemistry has been made either by use of a chiral starting material of known stereochemistry, by stereoselective synthesis of known stereochemistry or by biological activity.

Analytical Methods
HPLC-MS methods:

| Method: | 1 |
|---|---|
| Device: | Agilent 1200 with DA- and MS-Detector |
| Column: | Sunfire C18, 3 × 30 mm, 2.5 μm |
| Column Supplier: | Waters |

| Gradient/Solvent Time [min] | % Solvent [H$_2$O, 0.1% TFA] | % Solvent [Acetonitrile] | Flow [mL/min] | Temperature [° C.] |
|---|---|---|---|---|
| 0.00 | 97 | 3 | 2.2 | 60 |
| 0.20 | 97 | 3 | 2.2 | 60 |
| 1.20 | 0 | 100 | 2.2 | 60 |
| 1.25 | 0 | 100 | 3 | 60 |
| 1.40 | 0 | 100 | 3 | 60 |

| Method: | 2 |
|---|---|
| Device: | Agilent 1200 with DA- and MS-Detector |
| Column: | XBridge C18, 3 × 30 mm, 2.5 μm |
| Column Supplier: | Waters |

| Gradient/Solvent Time [min] | % Solvent [H$_2$O, 0.1% NH3] | % Solvent [Acetonitrile] | Flow [mL/min] | Temperature [° C.] |
|---|---|---|---|---|
| 0.00 | 97 | 3 | 2.2 | 60 |
| 0.20 | 97 | 3 | 2.2 | 60 |
| 1.20 | 0 | 100 | 2.2 | 60 |
| 1.25 | 0 | 100 | 3 | 60 |
| 1.40 | 0 | 100 | 3 | 60 |

| Method: | 3 |
|---|---|
| Device: | Waters Acquity with DA- and MS-Detector |
| Column: | Sunfire C18, 2.1 × 30 mm, 2.5 μm |
| Column Supplier: | Waters |

| Gradient/Solvent Time [min] | % Solvent [H$_2$O, 0.1% TFA] | % Solvent [Acetonitrile] | Flow [mL/min] | Temperature [° C.] |
|---|---|---|---|---|
| 0.00 | 99 | 1 | 1.5 | 60 |
| 0.02 | 99 | 1 | 1.5 | 60 |
| 1.00 | 0 | 100 | 1.5 | 60 |
| 1.10 | 0 | 100 | 1.5 | 60 |

| Method: | 4 |
|---|---|
| Device: | Waters Acquity with 3100 MS |
| Column: | XBridge C18, 3.0 × 30 mm, 2.5 μm |
| Column Supplier: | Waters |

| Gradient/Solvent Time [min] | % Solvent [H$_2$O, 0.1% NH$_3$] | % Solvent [Acetonitrile] | Flow [mL/min] | Temperature [° C.] |
|---|---|---|---|---|
| 0.0 | 95 | 5 | 1.5 | 60 |
| 1.3 | 1 | 99 | 1.5 | 60 |
| 1.5 | 1 | 99 | 1.5 | 60 |
| 1.6 | 95 | 5 | 1.5 | 60 |

| Method: | 5 |
|---|---|
| Device: | Waters Acquity with 3100 MS |
| Column: | Sunfire C18, 3.0 × 30 mm, 2.5 μm |
| Column Supplier: | Waters |

| Gradient/Solvent Time [min] | % Solvent [H$_2$O, 0.1% TFA] | % Sol [Acetonitrile 0.08% TFA] | Flow [mL/min] | Temperature [° C.] |
|---|---|---|---|---|
| 0.0 | 95 | 5 | 1.5 | 60 |
| 1.3 | 0 | 100 | 1.5 | 60 |
| 1.5 | 0 | 100 | 1.5 | 60 |
| 1.6 | 95 | 5 | 1.5 | 60 |

| Method: | 6 |
|---|---|
| Device: | Waters Acquity, QDa Detector |
| Column: | XBridge C18, 3 × 30 mm, 2.5 μm |
| Column Supplier: | Waters |

| Gradient/Solvent Time [min] | % Solvent [H$_2$O, 0.1% NH$_3$] | % Solvent [Acetonitrile] | Flow [mL/min] | Temperature [° C.] |
|---|---|---|---|---|
| 0.00 | 95 | 5 | 1.5 | 60 |
| 1.30 | 0 | 100 | 1.5 | 60 |
| 1.50 | 0 | 100 | 1.5 | 60 |

Synthesis of Intermediates

Intermediate 1

4-Methyl-3-[4-(1-methyl-1H-imidazol-5-yl)-1H-1,2,3-triazol-1-yl]benzoic acid

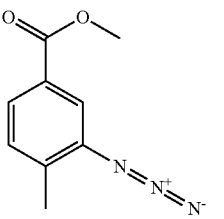

Step 1

-continued

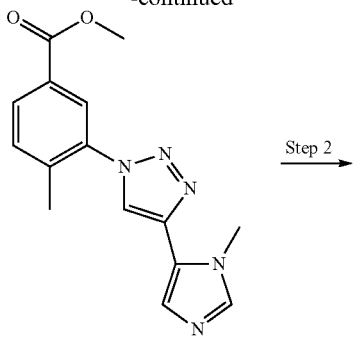

Step 2

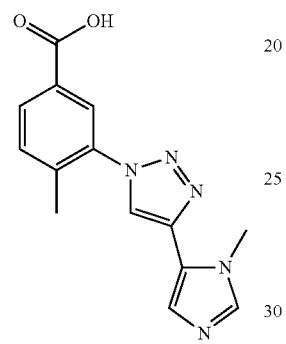

Step 1: Methyl 4-methyl-3-[4-(1-methyl-1H-imidazol-5-yl)-1H-1,2,3-triazol-1-yl] benzoate A solution of 5-ethynyl-1-methyl-1H-imidazole (425 mg) in methanol (10 mL) is added to a solution of methyl 3-azido-4-methylbenzoate (765 mg) in methanol (20 mL). Water (10 mL), copper(II) sulfate pentahydrate (45 mg) and sodium ascorbate (178 mg) are added and the resulting mixture is stirred at room temperature. After the reaction is complete the mixture is concentrated in vacuo and the residue is chromatographed on silica gel (dichloromethane/(1 M NH$_3$ in methanol) 100:0→96:4) to give the title compound.

Mass spectrum (ESI$^+$): m/z=298 [M+H]$^+$.

Step 2: 4-Methyl-3-[4-(1-methyl-1H-imidazol-5-yl)-1H-1,2,3-triazol-1-yl]benzoic acid The product from step 1 is dissolved in methanol (20 mL), 1 M aqueous NaOH (30 mL) is added and the mixture is stirred at room temperature for 4 h. 1 M aqueous HCl (10 mL) is added and the resulting precipitate is filtered off and dried in vacuo to give the title compound.

Mass spectrum (ESI$^-$): m/z=282 [M−H]$^+$.

The following intermediate is prepared in analogy to Intermediate 1 from the corresponding starting materials:

| Intermediate | Structure | Starting Materials | Analysis |
|---|---|---|---|
| 2 | 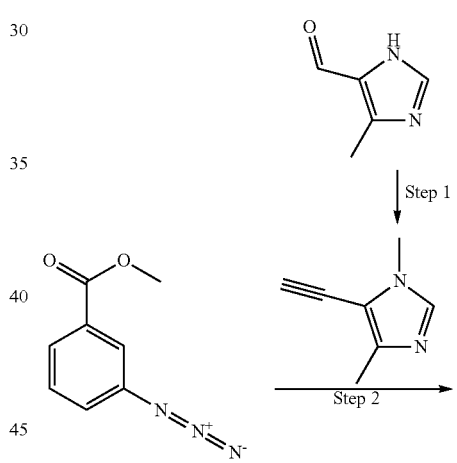 | methyl 3-azidobenzoate and 5-ethynyl-1-methyl-1H-imidazole | Mass spectrum (ESI$^-$): m/z = 268 [M − H]$^-$ |

Intermediate 3

Methyl 3-[4-(1,4-dimethyl-1H-imidazol-5-yl)-1H-1,2,3-triazol-1-yl]benzoate

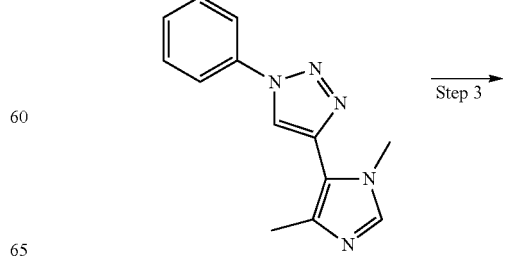

Step 3

-continued

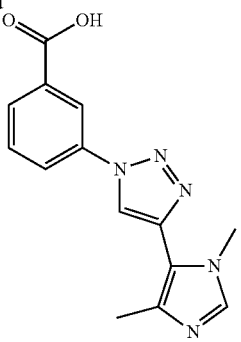

Step 1: 5-Ethynyl-1,4-dimethyl-1H-imidazole

A mixture of 4-methyl-1H-imidazole-5-carbaldehyde (5.0 g) and triphenylphosphine (13.0 g) in methanol (150 mL) is cooled in an ice/water bath and a solution of di-tert-butyl azodicarboxylate (13.0 g) in dichloromethane (100 mL) is added dropwise and the reaction mixture ist stirred for 2 h at room temperature. More triphenylphosphine (2.6 g) and di-tert-butyl azodicarboxylate (2.4 g) are added and the mixture is stirred for 1 h. The dichloromethane is evaporated from the mixture and $Cs_2CO_3$ (23.0 g) and dimethyl (1-diazo-2-oxopropyl)phosphonate (80%; 13 mL) are added (exothermal reaction, cooling is recommended!) and the mixture is stirred for 3 h at room temperature. Since conversion of starting material is still incomplete, $Cs_2CO_3$ (51.0 g) and dimethyl (1-diazo-2-oxopropyl)phosphonate (80%; 15 mL) in methanol (100 mL) are added in several portions under cooling during the following 24 h until conversion is complete. The mixture is filtered, the filtrate is diluted with methanol and water and acidified with 4 N aqueous HCl. Phases are separated and the aqueous phase is extracted with dichloromethane. The combined organic phases are extracted with water and the combined aqueous phases are basified with 10 N aqueous NaOH and extracted with dichloromethane. The combined organic phases are dried over $Na_2SO_4$, concentrated in vacuo, and the residue is chromatographed on silica gel ethyl acetate/cyclohexane (4:1) to give the title compound.

LC (Method 2): $t_R$=0.72 min; Mass spectrum (ESI$^+$): m/z=121 [M+H]$^+$.

Step 2: Methyl 3-[4-(1,4-dimethyl-1H-imidazol-5-yl)-1H-1,2,3-triazol-1-yl]benzoate Copper(II) sulfate pentahydrate (210 mg) and sodium ascorbate (990 mg) are added to a solution of methyl 3-azidobenzoate (0.5 M solution in tert-butyl methyl ether; 10 mL) and 5-ethynyl-1,4-dimethyl-1H-imidazole (500 mg) in methanol (27 mL) and water (13 mL). The resulting mixture is stirred at room temperature for 2 days. The mixture is diluted with ethyl acetate and 1 M aqueous NaOH, celite is added, the mixture is filtered and the phases are separated. The aqueous phase is washed with ethyl acetate/methanol (19:1) and the combined organic phases are dried over $Na_2SO_4$, concentrated in vacuo, and the residue is chromatographed on silica gel (dichloromethane/ (methanol/aqueous ammonia 25%/water=90:2:8) 19:1) to give the title compound.

Mass spectrum (ESI$^+$): m/z=298 [M+H]$^+$.

Step 3: 3-[4-(1,4-Dimethyl-1H-imidazol-5-yl)-1H-1,2,3-triazol-1-yl]benzoic acid The product from step 2 (420 mg) is dissolved concentrated hydrochloric acid (30 mL) and the mixture is stirred at 90° C. for 1.5 h. The mixture is concentrated in vacuo, triturated with diethyl ether, and dried to give the title compound as a hydrochloride salt.

Mass spectrum (ESI$^-$): m/z=282 [M−H]$^-$.

SYNTHESIS OF EXAMPLES

Example 1

4-Methyl-3-[4-(1-methyl-1H-imidazol-5-yl)-1H-1,2,3-triazol-1-yl]-N-[3-trifluoromethyl)phenyl]benzamide

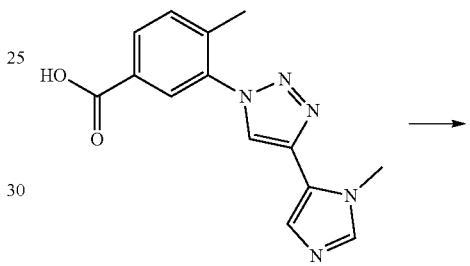

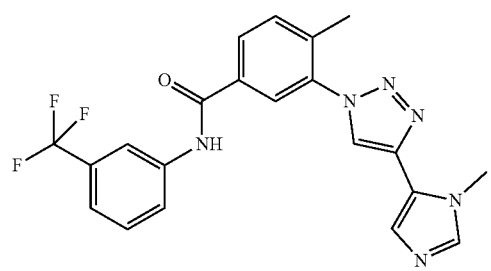

(3-Dimethylamino-propyl)-ethyl-carbodiimide (108 mg) is added to a mixture of 4-methyl-3-[4-(1-methyl-1H-imidazol-5-yl)-1H-1,2,3-triazol-1-yl]benzoic acid (80 mg), 3-trifluoromethyl-phenylamine (35 µL) and 4-dimethylaminopyridine (69 mg) in dichloromethane (2 mL). The reaction mixture is stirred at room temperature overnight. The solvent is evaporated in vacuo and the residue is purified by HPLC (water/acetonitrile/trifluoroacetic acid, water) to give the title compound.

LC (Method 1): $t_R$=0.91 min; Mass spectrum (ESI$^+$): m/z=427 [M+H]$^+$.

The following examples are prepared in analogy to Example 1, starting from the corresponding intermediates:

| Example | Structure | Starting Materials | Analysis |
|---|---|---|---|
| 3 | 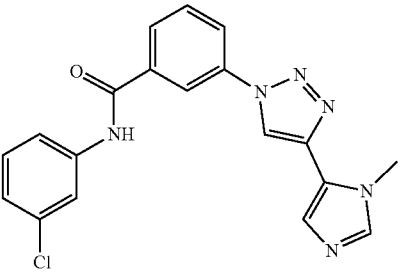 [SMILES: Cn1cncc1-c1cn(-c2cccc(C(=O)Nc3cccc(Cl)c3)c2)nn1] | Intermediate 2 and 3-chlorophenylamine | LC (Method 1): $t_R = 0.87$ min; Mass spectrum (ESI$^+$): m/z = 379 [M + H]$^+$ |
| 4 | 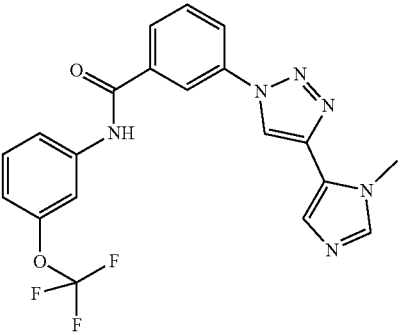 [SMILES: Cn1cncc1-c1cn(-c2cccc(C(=O)Nc3cccc(OC(F)(F)F)c3)c2)nn1] | Intermediate 2 and 3-trifluoromethoxyphenylamine | LC (Method 1): $t_R = 0.90$ min; Mass spectrum (ESI$^+$): m/z = 429 [M + H]$^+$ |
| 5 | 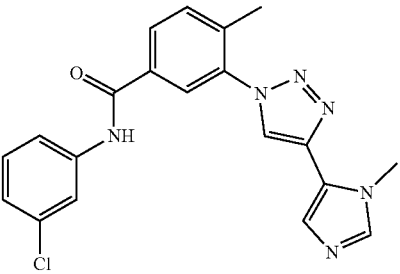 [SMILES: Cc1ccc(C(=O)Nc2cccc(Cl)c2)cc1-n1cc(-c2cncn2C)nn1] | Intermediate 1 and 3-chlorophenylamine | LC (Method 1): $t_R = 0.87$ min; Mass spectrum (ESI$^+$): m/z = 393 [M + H]$^+$ |
| 6 | 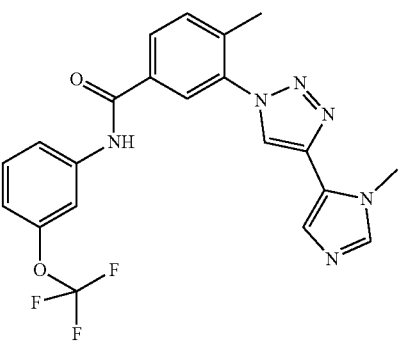 [SMILES: Cc1ccc(C(=O)Nc2cccc(OC(F)(F)F)c2)cc1-n1cc(-c2cncn2C)nn1] | Intermediate 1 and 3-trifluoromethoxyphenylamine | LC (Method 1): $t_R = 0.92$ min; Mass spectrum (ESI$^+$): m/z = 443 [M + H]$^+$ |

Example 2

3-[4-(1-Methyl-1H-imidazol-5-yl)-1H-1,2,3-triazol-1-yl]-N-[3-(trifluoromethyl)-phenyl]benzamide

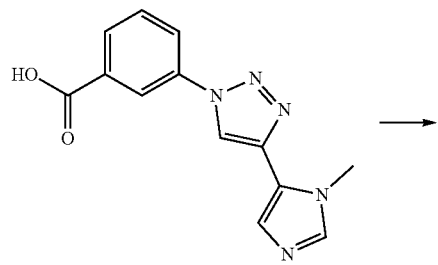

→

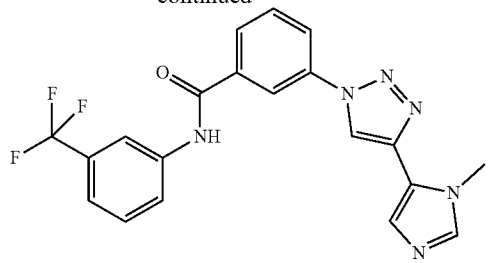

(3-Dimethylamino-propyl)-ethyl-carbodiimide (85 mg) is added to a mixture of 3-[4-(1-methyl-1H-imidazol-5-yl)-1H-1,2,3-triazol-1-yl]benzoic acid (60 mg), 3-trifluoromethyl-phenylamine (28 μL) and 4-dimethylaminopyridine (82 mg) in N,N-dimethylformamide (2 mL). The reaction mixture is stirred at room temperature overnight. The solvent is evaporated in vacuo and the residue is purified by HPLC (water/acetonitrile/trifluoroacetic acid) to give the title compound. LC (Method 1): $t_R$=0.89 min; Mass spectrum (ESI$^+$): m/z=413 [M+H]$^+$.

The following examples are prepared in analogy to Example 2, starting from the corresponding intermediates:

| Example | Structure | Starting Materials | Analysis |
|---|---|---|---|
| 7 | 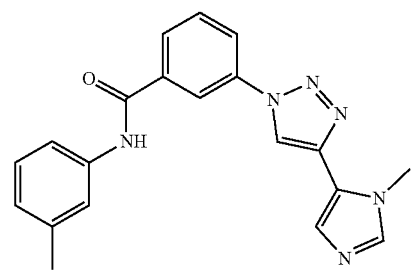 [SMILES: Cc1cccc(NC(=O)c2cccc(-n3cc(-c4cncn4C)nn3)c2)c1] | Intermediate 2 and 3-methyl-phenylamine | LC (Method 1): $t_R$ = 0.83 min; Mass spectrum (ESI$^+$): m/z = 359 [M + H]$^+$ |
| 9 | 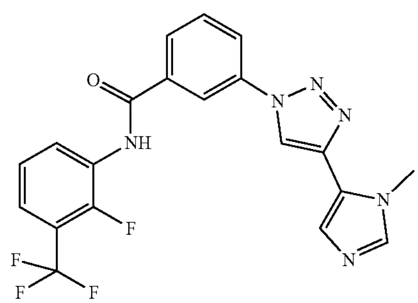 [SMILES: Cn1cncc1-c1cn(-c2cccc(C(=O)Nc3cccc(C(F)(F)F)c3F)c2)nn1] | Intermediate 2 and 2-fluoro-3-trifluoromethyl-phenylamine | LC (Method 1): $t_R$ = 0.88 min; Mass spectrum (ESI$^+$): m/z = 431 [M + H]$^+$ |
| 10 | 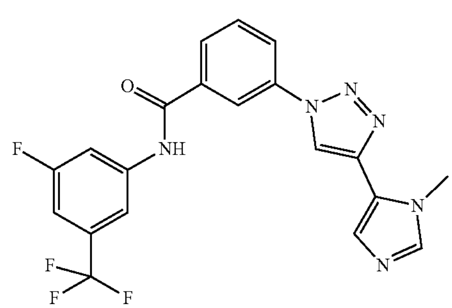 [SMILES: Cn1cncc1-c1cn(-c2cccc(C(=O)Nc3cc(F)cc(C(F)(F)F)c3)c2)nn1] | Intermediate 2 and 3-fluoro-5-trifluoromethyl-phenylamine | LC (Method 1): $t_R$ = 0.92 min; Mass spectrum (ESI$^+$): m/z = 431 [M + H]$^+$ |

| Example | Structure | Starting Materials | Analysis |
|---------|-----------|--------------------|----------|
| 11 | 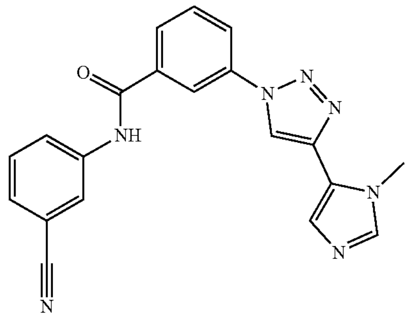 [SMILES: Cn1cncc1-c1cn(-c2cccc(C(=O)Nc3cccc(C#N)c3)c2)nn1] | Intermediate 2 and 3-amino-benzonitrile | LC (Method 1): $t_R$ = 0.80 min; Mass spectrum (ESI$^+$): m/z = 370 [M + H]$^+$ |
| 12 | 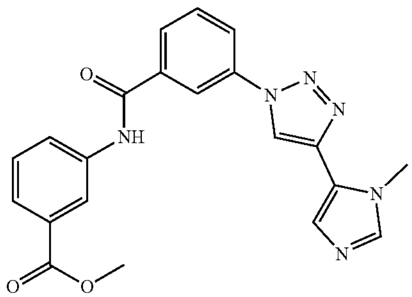 [SMILES: COC(=O)c1cccc(NC(=O)c2cccc(-n3cc(-c4cncn4C)nn3)c2)c1] | Intermediate 2 and 3-amino-benzoic acid methyl ester | LC (Method 3): $t_R$ = 0.47 min; Mass spectrum (ESI$^+$): m/z = 403 [M + H]$^+$ |
| 13 | 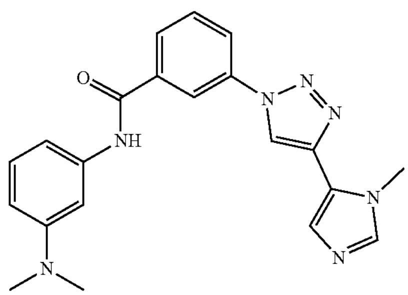 [SMILES: CN(C)c1cccc(NC(=O)c2cccc(-n3cc(-c4cncn4C)nn3)c2)c1] | Intermediate 2 and N,N-dimethylbenzene-1,3-diamine dihydrochloride | LC (Method 1): $t_R$ = 0.68 min; Mass spectrum (ESI$^+$): m/z = 388 [M + H]$^+$ |
| 14 | 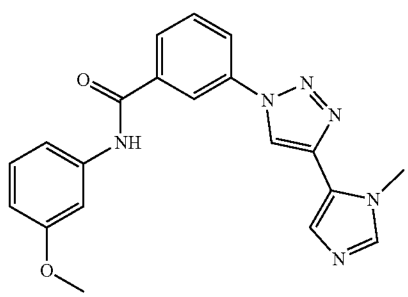 [SMILES: COc1cccc(NC(=O)c2cccc(-n3cc(-c4cncn4C)nn3)c2)c1] | Intermediate 2 and 3-methoxy-phenylamine | LC (Method 1): $t_R$ = 0.81 min; Mass spectrum (ESI$^+$): m/z = 375 [M + H]$^+$ |
| 15 | 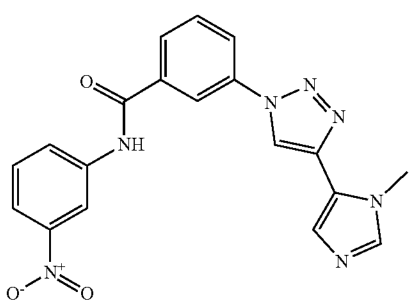 [SMILES: Cn1cncc1-c1cn(-c2cccc(C(=O)Nc3cccc([N+](=O)[O-])c3)c2)nn1] | Intermediate 2 and 3-nitro-phenylamine | LC (Method 3): $t_R$ = 0.48 min; Mass spectrum (ESI$^+$): m/z = 390 [M + H]$^+$ |

| Example | Structure | Starting Materials | Analysis |
|---|---|---|---|
| 16 | 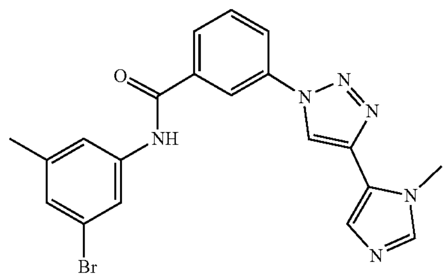 | Intermediate 2 and 3-bromo-5-methyl-phenyl-amine hydrochloride | LC (Method 1): $t_R$ = 0.92 min; Mass spectrum (ESI$^+$): m/z = 437 [M + H]$^+$ |

Example 8

3-[4-(1,4-Dimethyl-1H-imidazol-5-yl)-1H-1,2,3-triazol-1-yl]-N-[3-(trifluoromethyl)-phenyl]benzamide

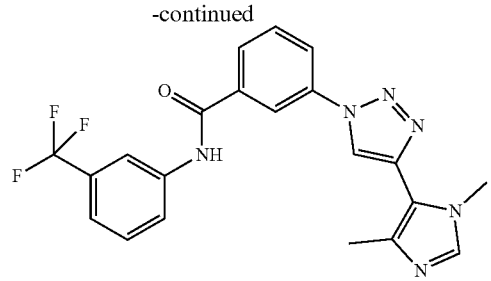

N,N-Diisopropylethylamine (220 μL) is added to a mixture of 3-[4-(1,4-dimethyl-1H-imidazol-5-yl)-1H-1,2,3-triazol-1-yl]benzoic acid hydrochloride (150 mg), (O-(7-azabenzotriazol-1-yl)-N,N,N',N'-tetramethyluronium-hexafluorophosphate (200 mg) and N,N-dimethylformamide (3 mL) and the mixture is stirred at room temperature for 30 min. 3-Trifluoromethyl-phenylamine (90 μL) is added and the reaction mixture is stirred at 50° C. for 2 h. The solvent is evaporated in vacuo and the mixture is purified by HPLC to give the title compound.

LC (Method 2): $t_R$=1.03 min; Mass spectrum (ESI$^+$): m/z=427 [M+H]$^+$.

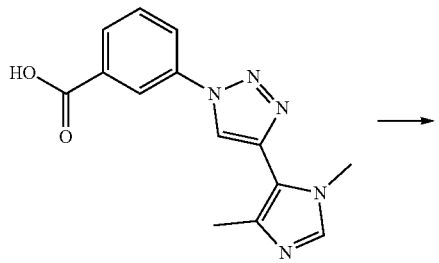

The following examples are prepared in analogy to Example 8, starting from the corresponding intermediates:

| Example | Structure | Starting Materials | Analysis |
|---|---|---|---|
| 17 | 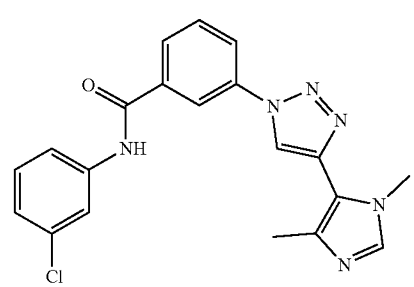 [SMILES: Cc1ncn(C)c1-c1cn(-c2cccc(C(=O)Nc3cccc(Cl)c3)c2)nn1] | Intermediate 3 and 3-chloro-phenylamine | LC (Method 4): $t_R$ = 0.80 min; Mass spectrum (ESI$^+$): m/z = 393 [M + H]$^+$ |

-continued

| Example | Structure | Starting Materials | Analysis |
|---|---|---|---|
| 18 | 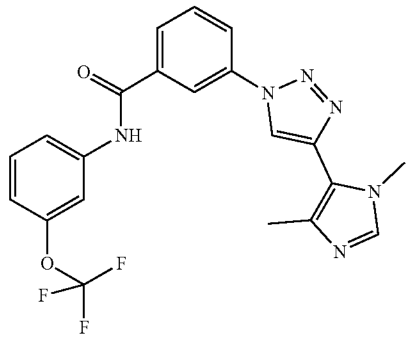 [SMILES: Cc1ncn(C)c1-c1cn(-c2cccc(C(=O)Nc3cccc(OC(F)(F)F)c3)c2)nn1] | Intermediate 3 and 3-methoxy-phenylamine | LC (Method 5): $t_R$ = 0.73 min; Mass spectrum (ESI⁺): m/z = 443 [M + H]⁺ |
| 19 | 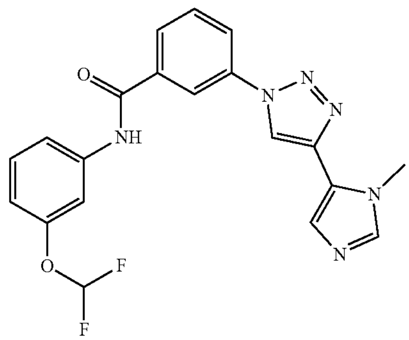 [SMILES: Cn1cncc1-c1cn(-c2cccc(C(=O)Nc3cccc(OC(F)F)c3)c2)nn1] | Intermediate 2 and 3-difluoromethoxy-phenylamine | LC (Method 6): $t_R$ = 0.72 min; Mass spectrum (ESI⁺): m/z = 411 [M + H]⁺ |
| 20 | 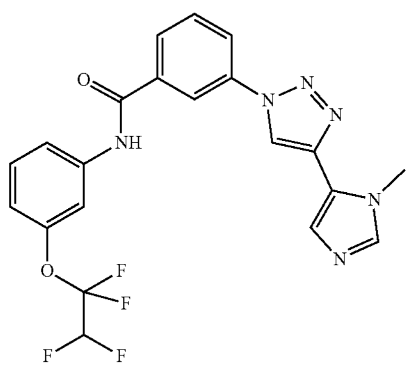 [SMILES: Cn1cncc1-c1cn(-c2cccc(C(=O)Nc3cccc(OC(F)(F)C(F)F)c3)c2)nn1] | Intermediate 2 and 3-(1,1,2,2-tetrafluoroethoxy)-phenylamine | LC (Method 6): $t_R$ = 0.80 min; Mass spectrum (ESI⁺): m/z = 461 [M + H]⁺ |

The invention claimed is:

1. A compound of formula (I)

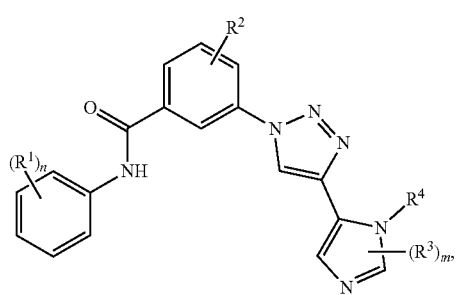

wherein $R^1$ is selected from the group consisting of F, Cl, Br, I, CN, NO₂, $C_{1-3}$-alkyl, —O—($C_{1-4}$-alkyl), —COOH, —C(=O)—O—($C_{1-4}$-alkyl), —NH₂, —NH($C_{1-3}$-alkyl) and —N($C_{1-3}$-alkyl)₂,
  wherein each alkyl group or sub-group is optionally substituted with 1 or more F atoms; and
  wherein multiple $R^1$ may be identical or different if n is 2;

$R^2$ is selected from the group consisting of H and $C_{1-3}$-alkyl;

$R^3$ is $C_{1-3}$-alkyl;

$R^4$ is $C_{1-3}$-alkyl;

n is an integer selected from 1 and 2; and m is an integer selected from 0 and 1;

wherein in any definition mentioned hereinbefore, if not specified otherwise, any alkyl group or sub-group may be straight-chained or branched and is optionally substituted with 1 or more F atoms, or a salt thereof.

2. The compound according to claim 1, wherein
$R^2$ is H or $CH_3$;
$R^3$ is $CH_3$; and
$R^4$ is $CH_3$;
or a salt thereof.

3. The compound according to claim 1, wherein
$R^1$ is independently of each other selected from the group consisting of F, Cl, Br, CN, $NO_2$, $C_{1-2}$-alkyl, —O—($C_{1-3}$-alkyl), —C(=O)—O—($C_{1-2}$-alkyl) and —N($C_{1-2}$-alkyl)$_2$,
wherein each alkyl group or sub-group is optionally substituted with 1 or more F atoms;
or a salt thereof.

4. The compound according to claim 1,
wherein
$R^1$ is independently of each other selected from the group consisting of F, Cl, Br, CN, $NO_2$, $CH_3$, —O—($C_{1-2}$-alkyl), —C(=O)—O—$CH_3$ and —N($CH_3$)$_2$,
wherein each alkyl group or sub-group is optionally substituted with one to three F atoms;
or a salt thereof.

5. The compound according to claim 1, wherein
$R^1$ is independently of each other selected from the group consisting of F, Cl, Br, CN, $NO_2$, $CH_3$, $CF_3$, —O—$CH_3$, —O—$CF_3$, —O—$CHF_2$, —O—$CF_2$—$CHF_2$, —C(=O)—O—$CH_3$ and —N($CH_3$)$_2$;
or a salt thereof.

6. The compound according to claim 1, wherein
$R^1$ is independently of each other selected from the group consisting of F, Cl, Br, $NO_2$, $CH_3$, $CF_3$, —O—$CF_3$ and —O—$CHF_2$;
or a salt thereof.

7. The compound according to claim 1, wherein
$R^2$ is H; or a salt thereof.

8. The compound according to claim 1, wherein
m is 1; or a salt thereof.

9. The compound according to claim 1 selected from the group consisting of:

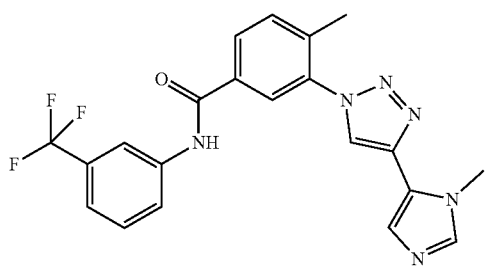

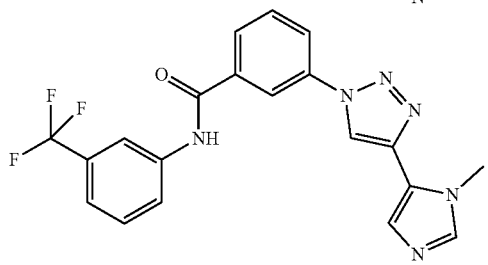

-continued

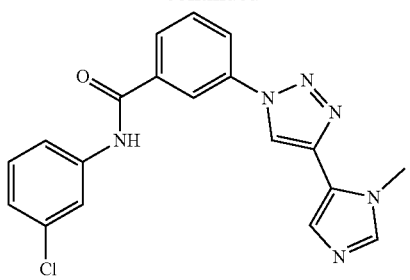

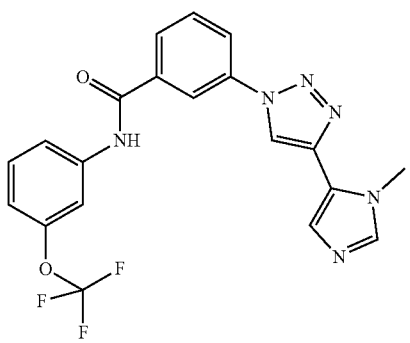

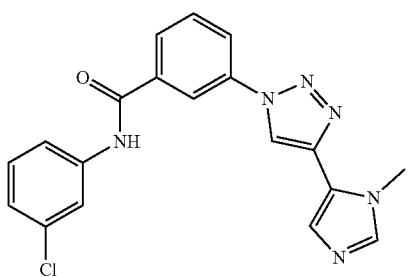

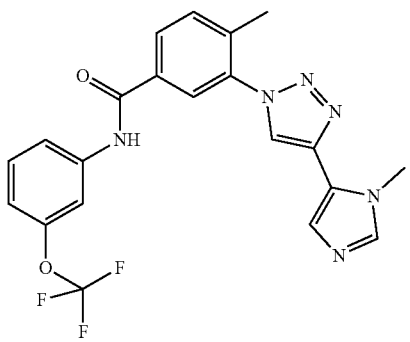

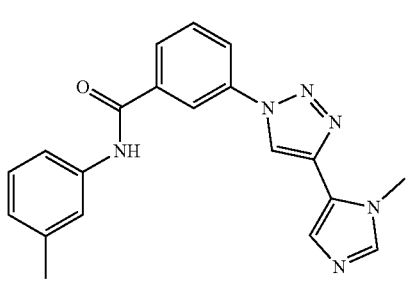

-continued
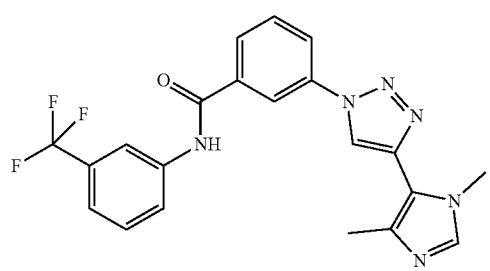
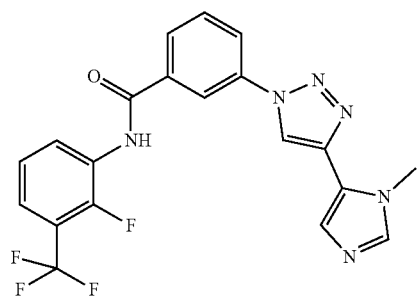
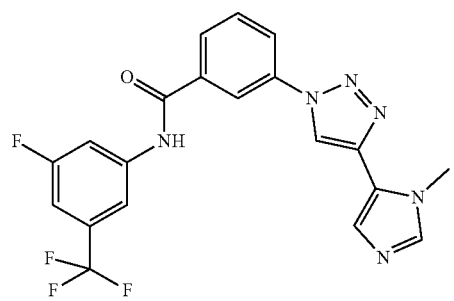
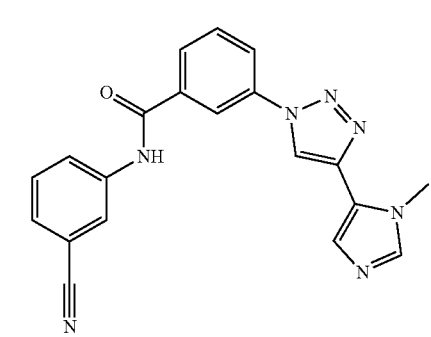
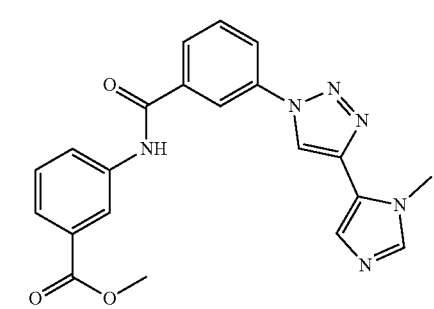
-continued
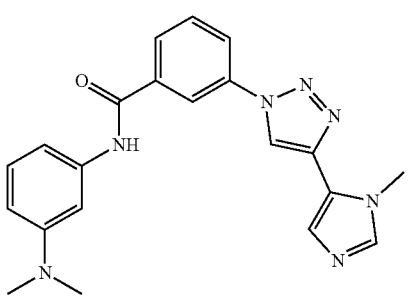
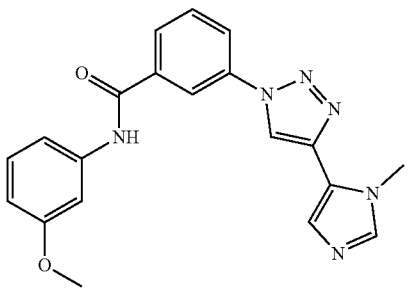
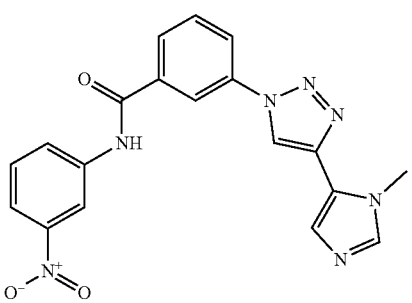
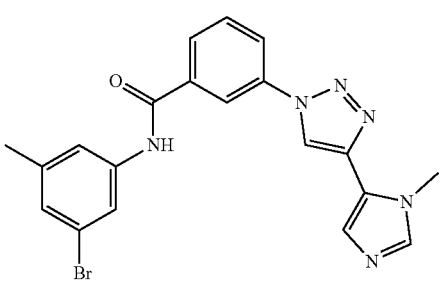
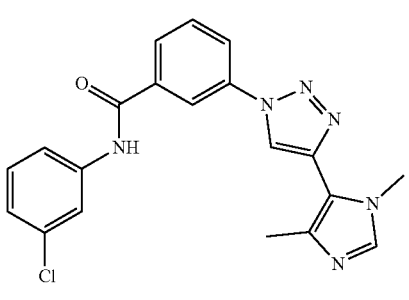

-continued

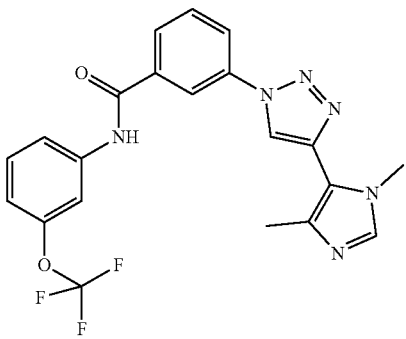

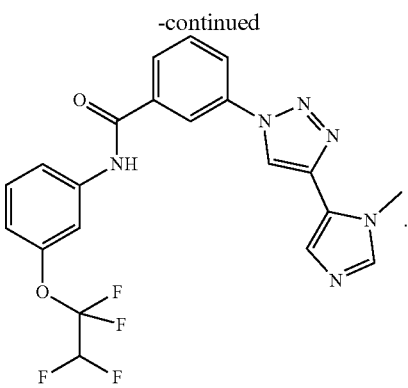

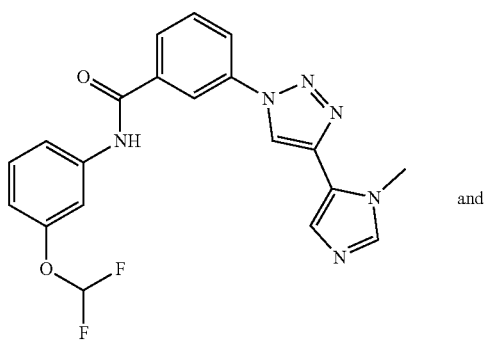

and or a salt thereof.

10. A pharmaceutically acceptable salt of a compound according to claim 1.

11. A method for treating type 2 diabetes, comprising administering a pharmaceutically effective amount of a compound according to claim 1, or a pharmaceutically acceptable salt thereof, to a patient in need thereof.

12. A pharmaceutical composition comprising a compound according to claim 1, or a pharmaceutically acceptable salt thereof, optionally together with one or more inert carriers and/or diluents.

13. A pharmaceutical composition comprising one or more compounds according to claim 1, or a pharmaceutically acceptable salt thereof, and one or more additional therapeutic agents, optionally together with one or more inert carriers and/or diluents.

14. A method for treating a disease or condition which is mediated by the activation of GPR142, comprising administering a pharmaceutically effective amount of a compound according to claim 1, or a pharmaceutically acceptable salt thereof, to a patient in need thereof.

\* \* \* \* \*